(12) United States Patent
Evans et al.

(10) Patent No.: US 12,186,525 B2
(45) Date of Patent: Jan. 7, 2025

(54) SYRINGE NEST

(71) Applicant: West Pharmaceutical Services, Inc., Exton, PA (US)

(72) Inventors: Christopher Evans, Long Valley, NJ (US); Brian Costello, Whitehouse Station, NJ (US); Raymond Protasiewicz, Whippany, NJ (US); Christopher Gieda, Long Valley, NJ (US); Jorge Santos, Scottsdale, AZ (US)

(73) Assignee: West Pharmaceutical Services, Inc., Exton, PA (US)

(*) Notice: Subject to any disclaimer, the term of this patent is extended or adjusted under 35 U.S.C. 154(b) by 492 days.

(21) Appl. No.: 17/134,848

(22) Filed: Dec. 28, 2020

(65) Prior Publication Data

US 2021/0113762 A1  Apr. 22, 2021

Related U.S. Application Data

(62) Division of application No. 16/071,622, filed as application No. PCT/US2017/015421 on Jan. 27, 2017, now abandoned.

(60) Provisional application No. 62/287,632, filed on Jan. 27, 2016.

(51) Int. Cl.
*A61M 5/00* (2006.01)
*B32B 3/12* (2006.01)

(52) U.S. Cl.
CPC .......... *A61M 5/008* (2013.01); *A61M 2207/10* (2013.01); *B32B 3/12* (2013.01)

(58) Field of Classification Search
CPC .................................................. A61M 5/008

USPC .......................................................... 206/364
See application file for complete search history.

(56) References Cited

U.S. PATENT DOCUMENTS

| 2,523,877 A | 9/1950 | Pestolesi |
| 3,918,920 A | 11/1975 | Barber |
| 3,997,057 A | 12/1976 | Craig |
| 4,038,149 A | 7/1977 | Liner et al. |
| 4,054,207 A | 10/1977 | Lazure et al. |
| 4,476,988 A | 10/1984 | Tanner |
| 4,510,119 A | 4/1985 | Hevey |
| 4,598,530 A | 7/1986 | Barnes et al. |
| 4,671,405 A | 6/1987 | Hagan |
| 4,722,440 A | 2/1988 | Johnston |
| 4,730,730 A | 3/1988 | Clarkson |
| 4,759,451 A | 7/1988 | Apps |

(Continued)

FOREIGN PATENT DOCUMENTS

| CN | 102470206 A | 5/2012 |
| DE | 102008046378 A1 | 3/2010 |

(Continued)

OTHER PUBLICATIONS

Office Action dated Feb. 27, 2018 in Japanese Design Application No. 2017-022003.

(Continued)

*Primary Examiner* — Jacob K Ackun
(74) *Attorney, Agent, or Firm* — Blank Rome LLP

(57) ABSTRACT

A syringe nest is provided that includes a planar base and a plurality of nesting units extending from and interconnected by the base. Each nesting unit includes a hollow hexagonal body having a first open end and an opposing second open end.

21 Claims, 25 Drawing Sheets

(56) References Cited

U.S. PATENT DOCUMENTS

| | | |
|---|---|---|
| 4,774,772 A | 10/1988 | Vetter et al. |
| 4,829,006 A | 5/1989 | Smith et al. |
| D302,207 S | 7/1989 | Matkovich |
| 4,867,315 A | 9/1989 | Baldwin |
| D332,664 S | 1/1993 | Sincock |
| 5,184,748 A | 2/1993 | Apps |
| 5,190,169 A | 3/1993 | Sincock |
| 5,372,252 A | 12/1994 | Alexander |
| D359,126 S | 6/1995 | Hovatter |
| 5,495,945 A | 3/1996 | Apps et al. |
| 5,579,929 A | 12/1996 | Schwartz |
| 5,589,137 A | 12/1996 | Markin et al. |
| 5,685,438 A | 11/1997 | Emanuel et al. |
| 5,695,057 A | 12/1997 | Sullivan |
| 5,961,086 A | 10/1999 | Moore et al. |
| 5,962,250 A | 10/1999 | Gavin et al. |
| 5,975,295 A | 11/1999 | Diamond |
| 6,019,225 A | 2/2000 | Kalmakis et al. |
| 6,098,802 A * | 8/2000 | Asa ............... B01L 9/543 206/443 |
| 6,164,449 A | 12/2000 | Lahti |
| 6,286,678 B1 | 9/2001 | Petrek |
| D454,202 S | 3/2002 | Pham et al. |
| 6,534,015 B1 | 3/2003 | Viot et al. |
| 6,971,518 B1 | 12/2005 | Lowry |
| D533,948 S | 12/2006 | Schaub et al. |
| 7,152,736 B1 | 12/2006 | Menichini |
| 7,232,038 B2 | 6/2007 | Whitney |
| 7,428,807 B2 * | 9/2008 | Vander Bush ....... A61M 5/002 422/23 |
| 7,431,157 B2 | 10/2008 | Porret et al. |
| 7,658,278 B2 | 2/2010 | Apps et al. |
| 7,942,264 B2 | 5/2011 | Friderich et al. |
| 7,963,396 B2 | 6/2011 | Vanderbush et al. |
| D645,156 S | 9/2011 | Reitze |
| 8,100,263 B2 | 1/2012 | Vanderbush et al. |
| 8,118,167 B2 | 2/2012 | Togashi et al. |
| 8,136,679 B2 | 3/2012 | Fry et al. |
| 8,142,740 B2 | 3/2012 | Self et al. |
| 8,196,741 B2 | 6/2012 | Finke et al. |
| 8,286,791 B2 | 10/2012 | Finke |
| D673,296 S | 12/2012 | Fry et al. |
| 8,360,238 B2 | 1/2013 | Nicoletti |
| 8,430,251 B2 | 4/2013 | Fry et al. |
| 8,453,838 B2 * | 6/2013 | Hill ............... A61M 5/008 211/74 |
| 8,485,357 B2 * | 7/2013 | Song ............... B01L 9/00 211/74 |
| D687,568 S | 8/2013 | Nakaji et al. |
| 8,522,975 B2 | 9/2013 | Finke et al. |
| 8,561,828 B2 | 10/2013 | Krauss et al. |
| 8,697,014 B2 | 4/2014 | Suzuki et al. |
| 8,794,442 B2 | 8/2014 | Nicoletti |
| 8,800,800 B2 | 8/2014 | Gerner et al. |
| 8,813,963 B2 | 8/2014 | Nicoletti |
| 8,939,288 B2 * | 1/2015 | Gagnieux ........... B65D 25/108 206/439 |
| D732,187 S | 6/2015 | Houkal et al. |
| 9,095,848 B2 * | 8/2015 | Carrel ............... B65D 71/70 |
| 9,156,598 B2 | 10/2015 | Nicoletti |
| 9,211,375 B2 | 12/2015 | Finke et al. |
| 9,403,619 B2 | 8/2016 | Deutschle et al. |
| 9,415,155 B2 * | 8/2016 | Togashi ............... A61M 5/008 |
| D768,873 S | 10/2016 | Stedman et al. |
| 9,468,587 B2 | 10/2016 | Lanier et al. |
| 9,468,711 B2 | 10/2016 | Iwase et al. |
| 9,545,635 B2 | 1/2017 | Motadel et al. |
| 9,555,911 B2 * | 1/2017 | Pawlowski ........... B65B 55/025 |
| 9,598,195 B2 | 3/2017 | Deutschle et al. |
| 9,623,171 B2 | 4/2017 | Okihara et al. |
| 9,630,745 B2 | 4/2017 | Lepot |
| D787,702 S | 5/2017 | Kawamura |
| 9,718,583 B2 | 8/2017 | Nicoletti et al. |
| 9,783,328 B2 | 10/2017 | Liversidge |
| D804,052 S | 11/2017 | Dadachanji et al. |
| 10,029,261 B2 | 7/2018 | Motadel et al. |
| 10,064,786 B2 | 9/2018 | Tsukiji |
| 10,064,787 B2 | 9/2018 | Deutschle et al. |
| 10,065,753 B2 | 9/2018 | Heath et al. |
| 10,086,131 B2 | 10/2018 | Okihara |
| 10,124,928 B2 | 11/2018 | Wissner et al. |
| 10,207,832 B2 | 2/2019 | Narvekar et al. |
| 10,227,161 B2 | 3/2019 | Auerbach |
| 10,287,056 B2 | 5/2019 | Wissner et al. |
| 10,336,479 B2 | 7/2019 | Deutschle et al. |
| 10,399,768 B2 | 9/2019 | Bertolin |
| 10,562,031 B2 | 2/2020 | Motadel et al. |
| 10,639,238 B2 | 5/2020 | Donschietz et al. |
| 10,703,539 B2 | 7/2020 | Deutschle et al. |
| 10,800,557 B2 | 10/2020 | Narvekar et al. |
| 10,874,473 B2 | 12/2020 | Togashi et al. |
| 10,918,784 B2 | 2/2021 | Yoshida |
| 10,919,043 B2 | 2/2021 | Johns et al. |
| 11,000,643 B2 | 5/2021 | Peruzzo |
| 2002/0170867 A1 | 11/2002 | Liu |
| 2005/0133386 A1 | 6/2005 | Wong |
| 2005/0139502 A1 | 6/2005 | Andersen et al. |
| 2007/0151882 A1 | 7/2007 | Cocheteux et al. |
| 2007/0272587 A1 | 11/2007 | Nguyen et al. |
| 2008/0000800 A1 | 1/2008 | Lamarche et al. |
| 2010/0012546 A1 * | 1/2010 | Togashi ............ B65D 25/108 206/534.1 |
| 2011/0192756 A1 | 8/2011 | Hill |
| 2012/0118777 A1 | 5/2012 | Kakiuchi et al. |
| 2012/0118903 A1 | 5/2012 | Norton et al. |
| 2013/0313143 A1 | 11/2013 | Finke et al. |
| 2014/0027333 A1 * | 1/2014 | Pawlowski ........... A61J 1/14 248/346.03 |
| 2015/0041349 A1 * | 2/2015 | Liversidge ........... B01L 9/54 206/364 |
| 2015/0089830 A1 | 4/2015 | Wissner et al. |
| 2015/0114871 A1 | 4/2015 | Fitzpatrick et al. |
| 2015/0122693 A1 | 5/2015 | Deutschle et al. |
| 2015/0166217 A1 * | 6/2015 | Deutschle ........... B32B 3/12 53/425 |
| 2015/0182686 A1 * | 7/2015 | Okihara ............ B65D 79/0084 206/365 |
| 2016/0121042 A1 | 5/2016 | Christensen |
| 2016/0332165 A1 | 11/2016 | Gunther |
| 2018/0134423 A1 | 5/2018 | Narvekar et al. |
| 2018/0193552 A1 | 7/2018 | Wright et al. |
| 2018/0208377 A1 | 7/2018 | Kloke et al. |
| 2018/0235838 A1 | 8/2018 | Kawamura |
| 2019/0070357 A1 | 3/2019 | Evans et al. |
| 2019/0083697 A1 | 3/2019 | Evans et al. |
| 2019/0298610 A1 | 10/2019 | Komann et al. |
| 2019/0343721 A1 | 11/2019 | Komann et al. |
| 2020/0156840 A1 | 5/2020 | Komann et al. |
| 2020/0253824 A1 | 8/2020 | Maritan et al. |
| 2020/0338258 A1 | 10/2020 | Standley |
| 2021/0178398 A1 | 6/2021 | Chiu et al. |
| 2021/0253279 A1 | 8/2021 | Dario |

FOREIGN PATENT DOCUMENTS

| | | |
|---|---|---|
| DE | 202012001250 U1 | 3/2012 |
| EP | 0035779 A1 | 9/1981 |
| EP | 0648685 A2 | 4/1995 |
| EP | 2125572 A2 | 12/2009 |
| EP | 1449551 B1 | 4/2011 |
| EP | 2461849 A1 | 6/2012 |
| EP | 2659981 A1 | 11/2013 |
| EP | 2872843 A1 | 5/2015 |
| EP | 2886983 A1 | 6/2015 |
| EP | 2890423 A1 | 7/2015 |
| EP | 3244945 A2 | 11/2017 |
| EP | 3329997 A1 | 6/2018 |
| FR | 2899482 A1 | 10/2007 |
| JP | 2014-238251 A | 12/2014 |
| JP | 2015-528344 A | 9/2015 |
| WO | 2008067467 A2 | 6/2008 |
| WO | 2010086128 A1 | 8/2010 |

(56) References Cited

FOREIGN PATENT DOCUMENTS

| WO | 2011/015896 A1 | 2/2011 |
| WO | 2013031264 A1 | 3/2013 |
| WO | 2014/009037 A1 | 1/2014 |
| WO | 2014/033766 A1 | 3/2014 |
| WO | 2016/115477 A2 | 7/2016 |

OTHER PUBLICATIONS

Office Action dated Feb. 27, 2018 in Japanese Design Application No. 2017-022004.
Office Action dated Feb. 27, 2018 in Japanese Design Application No. 2017-022005.
Office Action dated Feb. 27, 2018 in Japanese Design Application No. 2017-022006.
Int'l Search Report issued May 9, 2017 in Int'l Application No. PCT/US2017/015421.
Written Opinion issued Jan. 17, 2018 in Int'l App. No. PCT/US17/15421.
Office Action dated Apr. 6, 2018 in U.S. Appl. No. 29/599,488.
Office Action dated Mar. 22, 2018 in U.S. Appl. No. 29/599,487.
Office Action dated Mar. 22, 2018 in U.S. Appl. No. 29/599,492.
Office Action dated Mar. 29, 2018 in U.S. Appl. No. 29/599,490.

* cited by examiner

SYRINGE NEST

CROSS-REFERENCE TO RELATED APPLICATION SECTION

This application is a Divisional Application of U.S. patent application Ser. No. 16/071,622 filed Jul. 20, 2018 which is a section 371 of International Application No. PCT/US17/15421, filed Jan. 27, 2017, which was published Aug. 3, 2017 under International Publication No. WO 2017/132554 A1, which claims the benefit of U.S. Provisional Application No. 62/287,632, filed Jan. 27, 2016, the disclosures of which are incorporated herein by reference.

BACKGROUND OF THE INVENTION

The present invention relates to a syringe nest. In particular, the present invention relates to a syringe nest of such a geometry that a plurality of syringes may be securely individually nested in chimneys in close proximity to each other, without compromising injection mold tool integrity.

A syringe nest is typically a substantially planar tray which sits in a syringe tub and has a plurality of individual nesting units, typically referred to as chimneys, each capable of receiving a syringe, to contain, transport and fill syringes in various manufacturing processes. The syringe nest is typically used in automation processes for the assembly of, for example, pre-filled syringes. The chimneys of a syringe nest have a defined center to center distance that must remain accurate, in order to ensure that the nest is compatible with existing manufacturing, packaging, and filling equipment. The quantity sizes of syringe nests have been increasing in recent years, with 160 chimneys/nest potentially becoming the new standard.

This has caused the syringe chimneys to be formed significantly closer together, particularly for nests requiring larger chimney diameters due to integrated safety systems. As the standard circular chimneys get closer together, moldability of such nests may become impossible and/or injection mold geometry may become thinner and less robust. In turn, manufacturing cycle time is increased and the mold life is reduced.

Accordingly, there is a need for a syringe nest with chimneys that meet the standard requisite center to center distance, but which can be optimized for injection molding.

In accordance with one embodiment, the present invention relates to a syringe nest having a hexagonal structure that enables more robust mold geometry, but which also preserves manufacturer-specified center to center distance of nest chimneys and syringes, such that the nest is acceptable for use in existing automation and filling equipment. In another embodiment, the present invention also relates to a syringe nest which reduces or eliminates the troublesome and unpredictable warping condition that syringe nests may exhibit post sterilization procedures (e.g., by gamma irradiation, ethylene oxide, autoclaving, etc.).

BRIEF SUMMARY OF THE INVENTION

Briefly stated, in one embodiment, the present invention relates to a syringe nest comprising a planar base and a plurality of nesting units extending from and interconnected by the base. Each nesting unit comprises a hollow hexagonal body having a first open end and an opposing second open end.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1A:
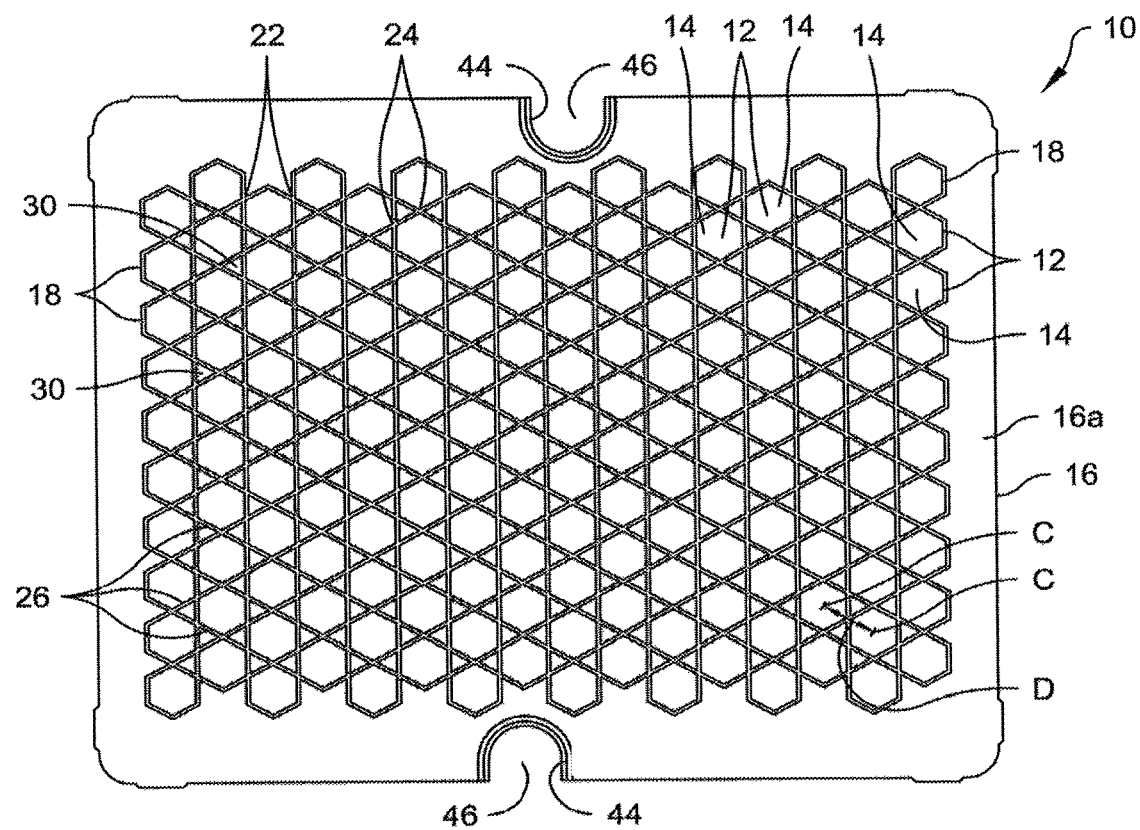
FIG. 1A is a top plan view of a syringe nest in accordance with an embodiment of the present invention.

Reference will now be made in detail to the present embodiments of the invention illustrated in the accompanying drawings. It should be noted that the drawings are in simplified form and are not drawn to precise scale. Certain terminology is used in the following description for convenience only and is not limiting. The words "right," "left," "top," "bottom" and "lower" designate directions in the drawings to which reference is made. The words "first," "second," "third" and "fourth" designate an order of operations in the drawings to which reference is made, but do not limit these steps to the exact order described. The words "inwardly" and "outwardly" refer to directions toward and away from, respectively, the geometric center of the device and designated parts thereof. Unless specifically set forth herein, the terms "a," "an" and "the" are not limited to one element, but instead should be read as meaning "at least one." The terminology includes the words noted above, derivatives thereof and words of similar import.

Figure 6A:
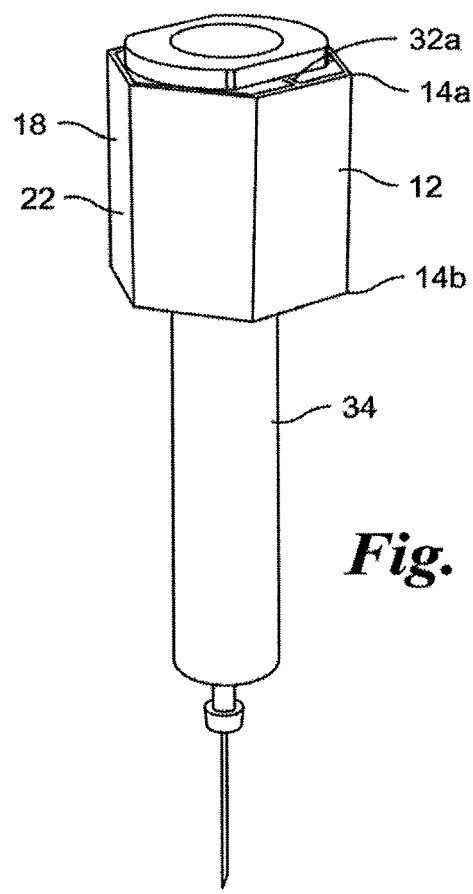
FIG. 6A is a top perspective view of a single chimney of the syringe nest of FIG. 4A with a syringe arranged therein.
Figure 6B:
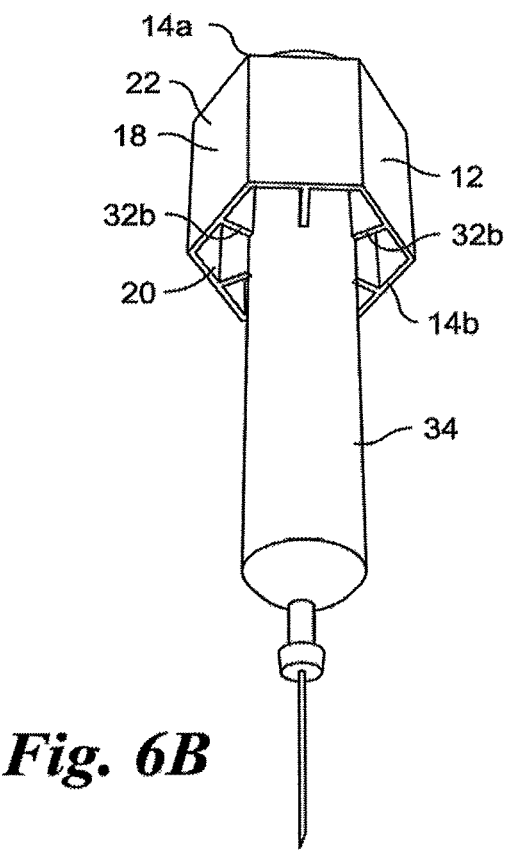
FIG. 6B is a bottom perspective view of a single chimney of the syringe nest of FIG. 4A with a syringe arranged therein.

Referring to the drawings in detail, wherein like numerals and characters indicate like elements throughout, there are shown in FIGS. 1A-23E, presently preferred embodiments of syringe nests in accordance with the present invention. With reference initially to FIGS. 1A-3, the syringe nest, generally designated 10, includes a plurality of single nesting units, referred to herein as chimneys, 12. The nest 10 can include a syringe 34 (e.g., see FIGS. 6A-6C) received within each of the plurality of chimneys 12.

The nest 10 is generally configured as a planar tray. While the present embodiment is configured with the nest 10 configured as a planar square tray, the nest 10 can alternatively be configured into any planar fashion suitable for its intended use, such as a planar circular, rectangular, oval, or octagonal shaped tray.

Figure 1B:
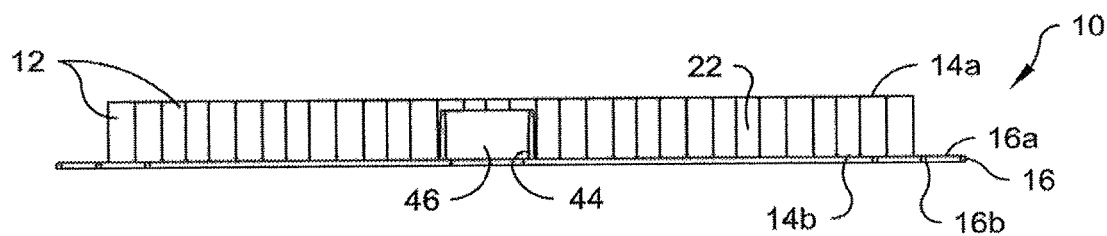
FIG. 1B is a side elevational view of the syringe nest of FIG. 1A.
Figure 2:
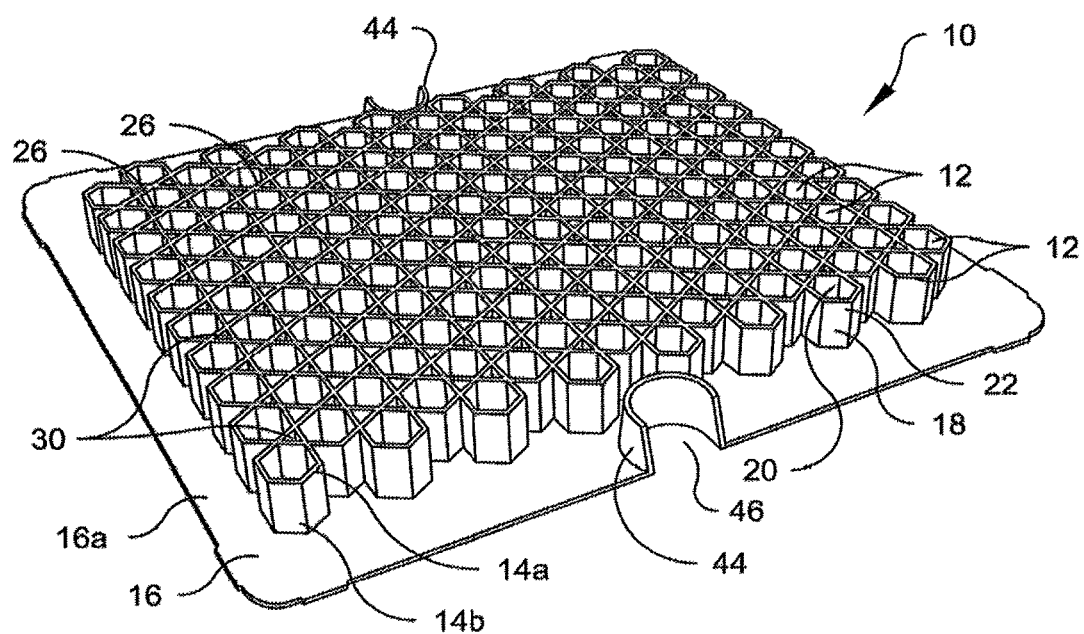
FIG. 2 is a side perspective view of the syringe nest of FIG. 1A.
Figure 3:
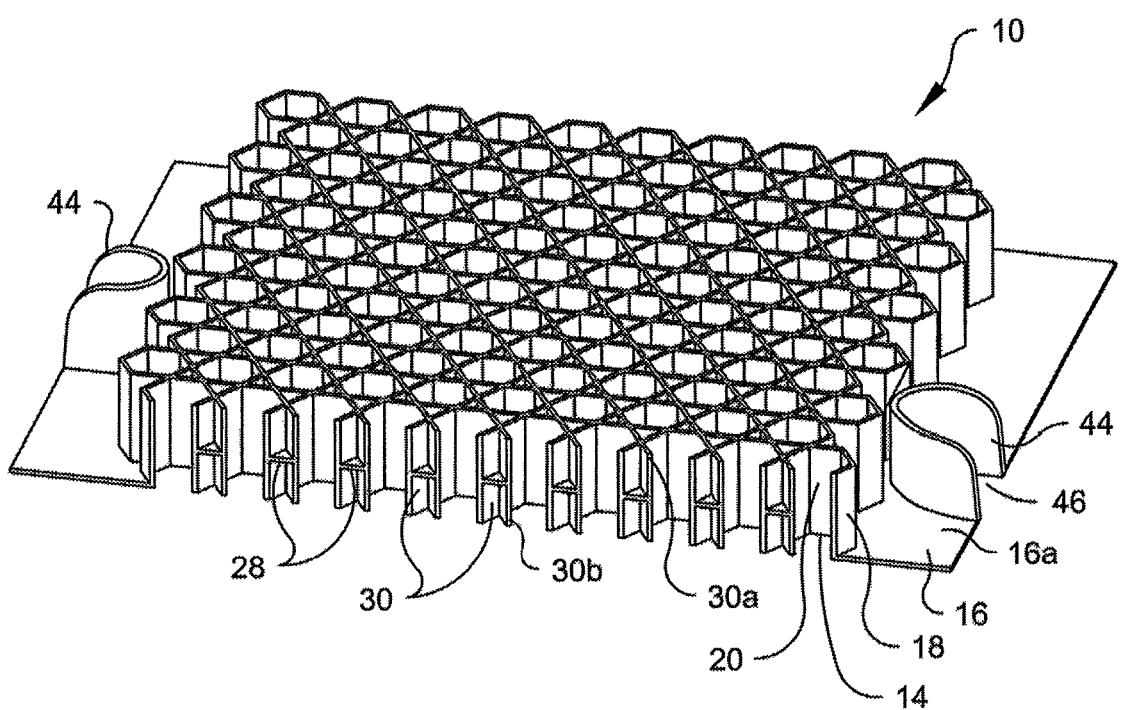
FIG. 3 is a sectional side perspective view of the syringe nest of FIG. 1A.

Referring to FIGS. 1A-1B, the nest includes a base 16 having a first surface 16a and an opposing second surface 16b. Each chimney 12 includes a generally hollow body 14 that extends distally from the first surface 16a of the base 16. The hollow body 14 includes a first open end 14a distal from the base 16 and a second open end 14b proximate the base 16. The hollow body 14 also includes a generally smooth interior wall surface 20 and an exterior wall surface 22.

Referring to FIGS. 1A-1B and 2-3, in a first embodiment, each of the chimneys 12 preferably has a hexagonal shape or geometry. Thus, each chimney 12 has six sidewalls 18 and six connecting lines (also known as vertices or corners) 24. The hexagonal chimneys 12 are aligned symmetrically in a point to point, vertex to vertex, or corner to corner orientation. That is, the chimneys 12 are interconnected in such a manner that each line/vertex/corner 24 of one chimney 12 also forms the line/vertex/corner 24 of another chimney 12. Each chimney 12 thus shares at least one line/vertex/corner 24 with at least one other chimney 12. More preferably, except for the perimeter chimneys 12, every line/vertex/corner 24 of each chimney 12 is common to that of another chimney 12. Thus, each chimney 12 shares a common line/vertex/corner 24 with two or more other chimneys 12.

Hexagonal chimneys 12 arranged in the line to line orientation naturally also form contiguous walls 26 that are advantageous for injection molding. Circular chimneys, as shown in the prior art nest of FIG. 15, would not allow for contiguous walls to be made without creating geometry that is disadvantageous to injection molding, namely a thin walled tool geometry. The geometry of the nest 10 according to the first preferred embodiment allows for maintaining a predetermined center to center distance D (e.g., as required by manufacturers), that is a predetermined distance D between a center C of one chimney 12 and a center C of an adjacent chimney 12, without excessive sidewall 18 thickness.

The line to line arrangement of the hexagonal chimneys 12 naturally creates voids 30, and more particularly triangular-shaped voids 30, between chimneys 12. It will be understood by those skilled in the art that the voids 30 may have any shape based on the shape of the chimneys 12. In one aspect, in order to further enhance moldability and reduce manufacturing cycle time, an intermediate wall 28 is provided between the first and second open ends 30a, 30b of each of the triangular voids 30 (best seen in FIG. 3). The intermediately wall 28 preferably has a shape that conforms with the geometric shape of the void 30 (e.g., a triangular shaped intermediate wall 28). The intermediate wall 28 is horizontally-oriented (i.e., perpendicular to the direction in which the body 14 of each chimney 12 extends). Such walls 28 allow for more shallow injection molding draws and increase mold robustness.

In a second preferred embodiment, the plurality of hexagonal chimneys 12 are arranged in a honeycomb pattern, in order to maintain the predetermined center to center distance D of the chimneys 12, and more particularly the predetermined center to center distance D between the syringes to be placed within each chimney 12 (FIGS. 4A-6C). That is, the chimneys 12 are interconnected in such a manner that at least one sidewall 18, and preferably each sidewall 18, of one chimney 12 also forms a sidewall 18 of another chimney 12 (i.e., contiguous walls), such that no triangular or other voids are formed between adjacent chimneys 12. Each chimney 12 thus shares at least one sidewall 18 with at least one other chimney 12. More preferably, with the exception of the outer peripheral chimneys 12, every sidewall 18 of each chimney 12 is common to that of another chimney 12.

Thus, each chimney 12 shares a common sidewall 18 with a plurality of other chimneys 12.

Conventionally, utilizing solely a honeycomb structure based on the desired center to center chimney distance would require excessive wall thickness to form a platform on which flanges of the syringes may rest, which would be disadvantageous for injection molding. The second preferred embodiment of the present invention avoids such excess wall thickness. In particular, each of the hexagonal chimneys 12 has a relatively large diameter that enables maintaining the predetermined center to center distance D, but also does not have an excessive sidewall 18 thickness. Accordingly, the diameter Dc of each chimney 12 is generally larger than the diameter of the flange of the syringe 34. As such, the syringe flange cannot rest on the chimney sidewalls 18.

In the embodiments shown in FIGS. 1A-6C, the entirety of the body 14 of each chimney 12 is positioned on one side of the planar base 16, namely on the first surface 16a of the base 16. In another embodiment, as shown in FIGS. 19-21B, a first portion of the body 14 extends distally from the first surface 16a of the base 16 and a second portion of the body 14 extends distally from the second surface 16b of the base 16. In other words, the base 16 is positioned at an intermediate point between the first open end 14a and the second open end 14b of each hollow body 14. Preferably, the base 16 is positioned at a geometric center point between the first and second ends 14a, 14b, but it will be understood that the base 16 may be located at any position between the two ends 14a, 14b.

As such, the base 16 essentially serves as a peripheral flange that extends in a midline plane of the plurality of chimneys 12, and which provides strength and stiffness to the nest 10 to reduce warping effects which occur during molding (e.g., by facilitating consistent cooling), post molding (e.g., by facilitating more uniform shrinkage), and sterilization (e.g., by providing a robust geometry that is more resistant to sterilization temperatures). The peripheral flange 16 also further enhances moldability and reduces injection molding cycle time, allowing for more shallow draws and increased mold robustness.

In one embodiment, for example as shown in FIGS. 19-21B, the nest 10 further includes a plurality of reinforcing members or stiffening members 42. Preferably, a plurality of stiffening members 42 are provided on the first surface 16a and on the second surface 16b of the base 16. More preferably, the stiffening member 42 are provided on the perimeter of the first and second surfaces 16a, 16b of the base 16 surrounding the plurality of chimneys 12. In one embodiment, the stiffening members 42 are elongated stiffening ribs 42, each of which has a first end 42a proximate a chimney 12 and an opposing second end 42b proximate an edge of the base 16. Preferably, each stiffening rib 42 extends at an angle from the peripheral edge of the base 12 toward the chimneys 12 to provide stiffness and strength to the base 12.

In one embodiment, an arcuate shaped edge ridge 44 also extends generally perpendicularly from the planar base 16 and defines an edge hole 46 (see, e.g., FIGS. 1A-3 and 19-20). In another embodiment, portions of the planar base 16 are merely recessed or indented to form the edge holes 46 (see, e.g., FIGS. 4A-5). One or more edge holes 46 are preferably included in the base 16 such that a user is able to insert a finger or tool through the edge holes 46 for ease of gripping. The edge rib 44 (if present) provides stiffness and strength for the base 16 proximate the edge holes 46. The edge holes 46 and edge rib 44 are not limited to inclusion in the edge of the base 16 and may be instead positioned at nearly any location on the base 16.

Figure 4A:
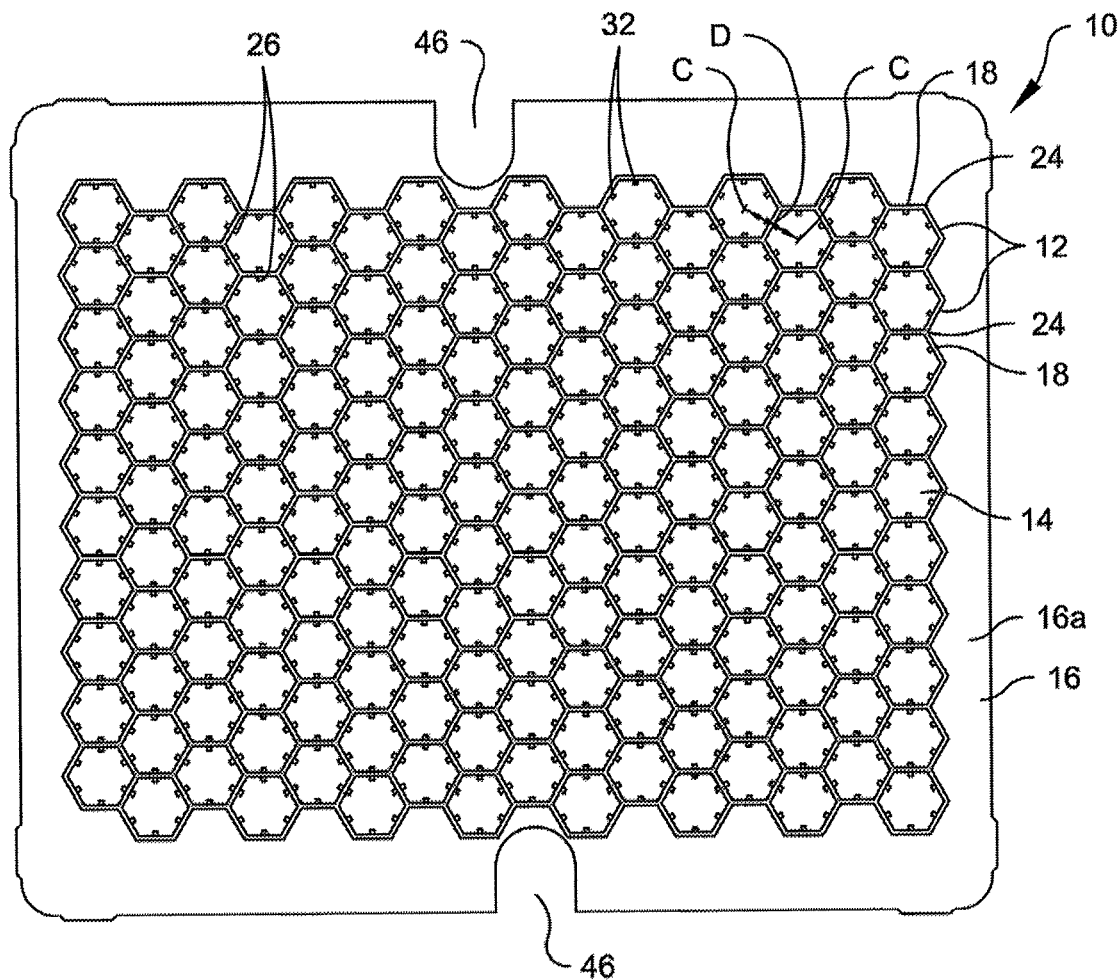
FIG. 4A is a top plan view of a syringe nest in accordance with another embodiment of the present invention.
Figure 4B:
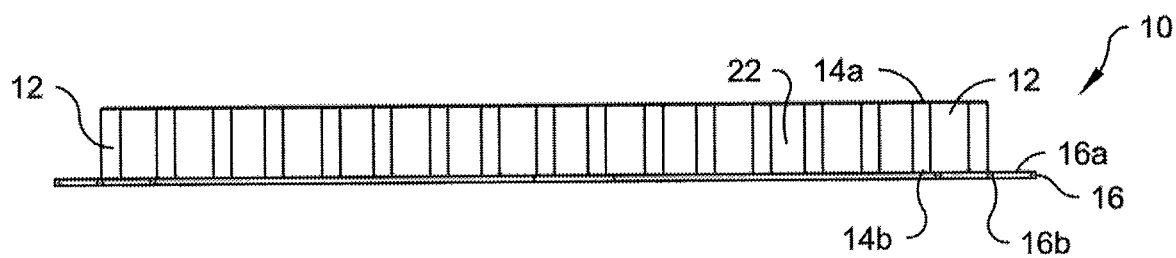
FIG. 4B is a side elevational view of the syringe nest of FIG. 4A.
Figure 5:
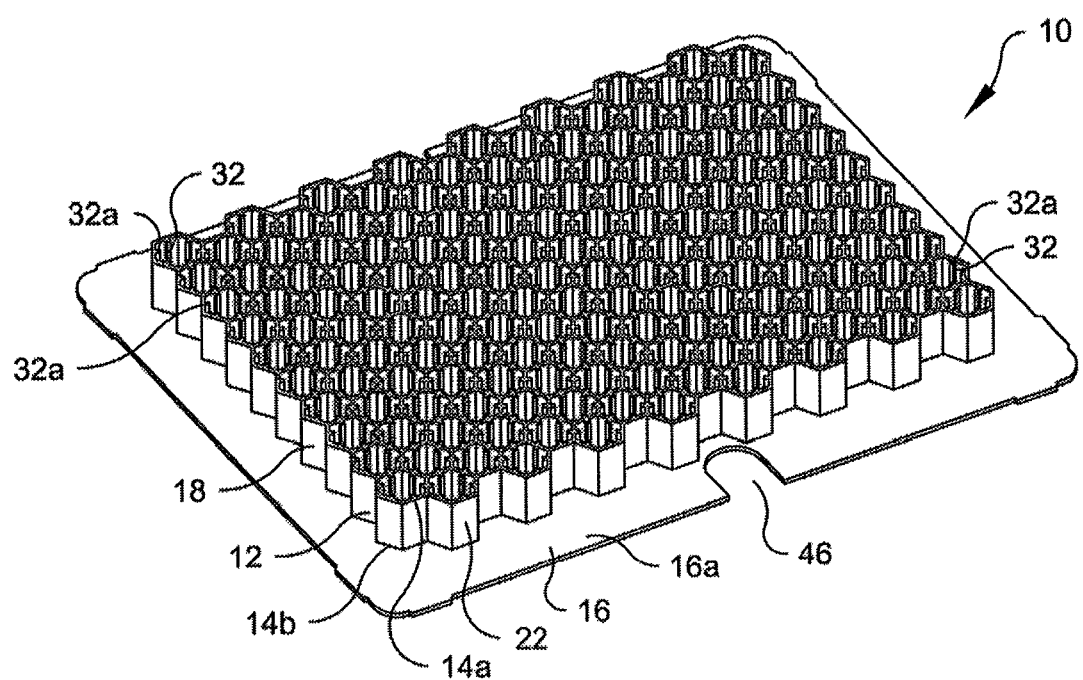
FIG. 5 is a side perspective view of the syringe nest of FIG. 4A.
Figure 6C:
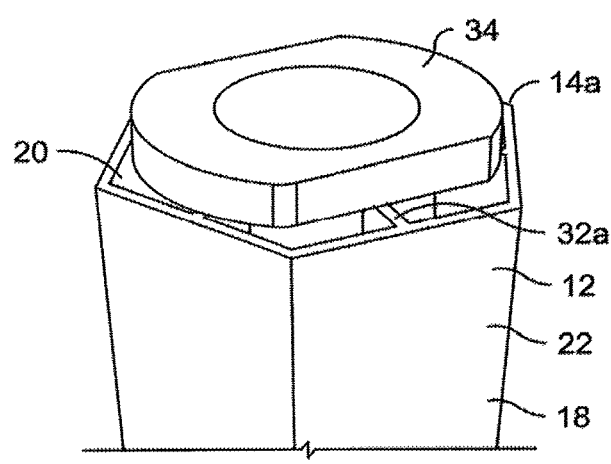
FIG. 6C is a top perspective, partial view of a single chimney of the syringe nest of FIG. 4A with a syringe arranged therein.

In one embodiment, to prevent the syringe from falling through the chimney 12, while also keeping each syringe 34 centered within a respective chimney 12 (i.e., a concentric arrangement) and preventing excessive movement of the syringe 34 within the chimney 12, at least one chimney 12, and more preferably a plurality of the chimneys 12, each includes at least one retention member 32, and more preferably a plurality of retention members 32 (see FIGS. 4 and 6C). Each retention member 32 is preferably a radially inwardly extending member. For example, each retention member 32 may be configured as a longitudinally extending rib formed on the interior wall surface 20 of each chimney 12. The retention members 32 may alternatively be configured as an annular rib, a flange, a flange-like rib, bumps, walls, shelves, pegs or the like extending from one or more of the internal surface 20 of the hexagonal chimney 12 sidewalls 18 proximate the first distal end 14a.

Figure 10:
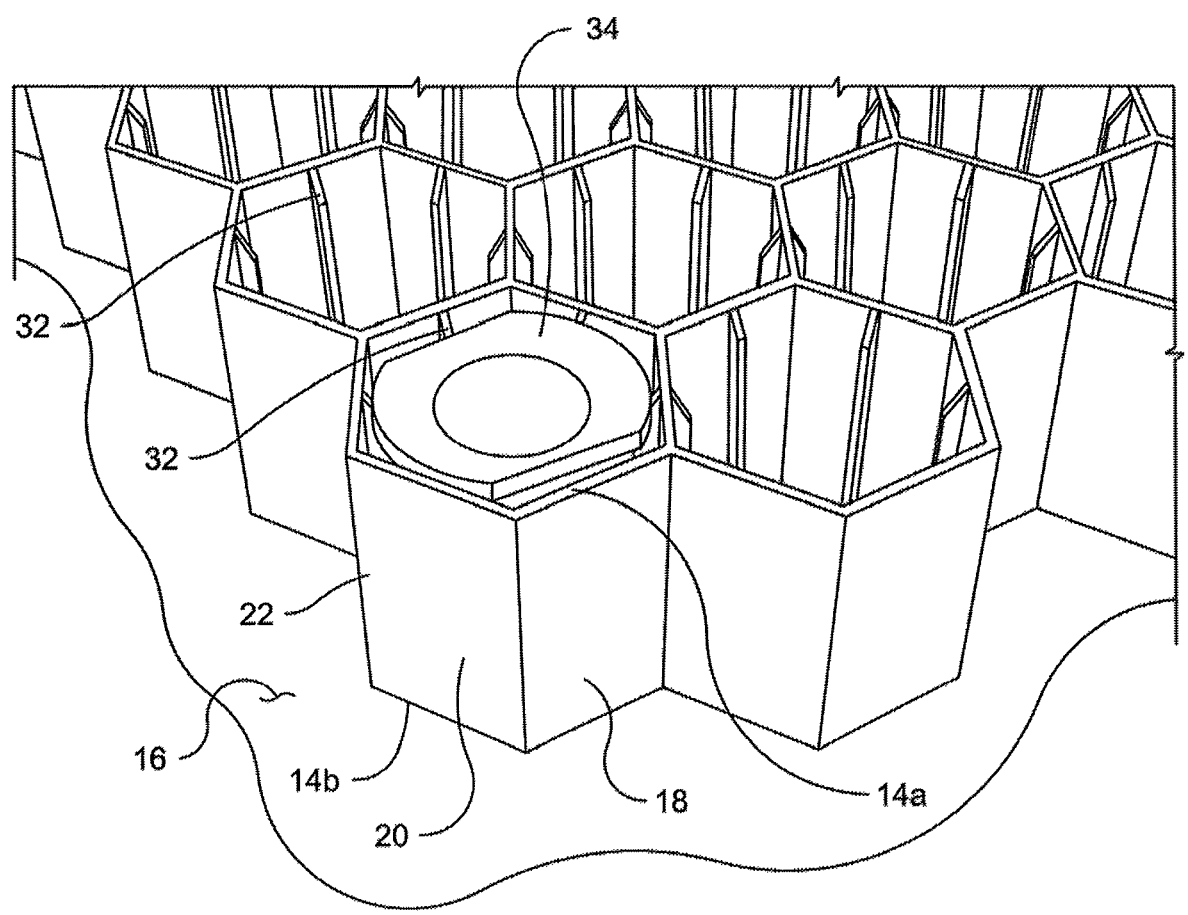
FIG. 10 is a top perspective, partial view of a syringe nest in accordance with another embodiment of the present invention with a syringe arranged in one chimney.

In the present embodiment, as shown in FIGS. 4-6C, each retention member 32 is in the form of a longitudinally extending rib that extends from the first distal end 14a of each chimney 12 toward the second proximal end 14b. Each rib 32 thus has a first end 32a proximate the first distal end 14a of each chimney 12 and a second end 32b proximate the second proximal end 14b of each chimney 12. As such, in use, the syringe 34 flange rests on the exposed surface (i.e., the first end 32a) of the one or more retention members 32 above the plane of the first distal end 14a of each chimney 12, as shown in FIGS. 6A and 6C. Preferably, each rib 32 extends along an entire height or length of each chimney 12 (i.e., from the first distal end 14a to the second proximal end 14b), but it will be understood that each rib 32 need not extend all the way to the second proximal end 14b. In another embodiment, as shown in FIG. 10, one or more ribs 32, and more preferably each rib 32, may be chamfered (preferably at the first end 32a), to assist in centering the syringe 34 within a respective chimney 12 and keeping the syringe 34 flange contained therein. Such a configuration may also prevent catching a safety system (not shown) on the chamfered ribs 32 during insertion of a syringe 34 into a chimney 12.

Figure 7:
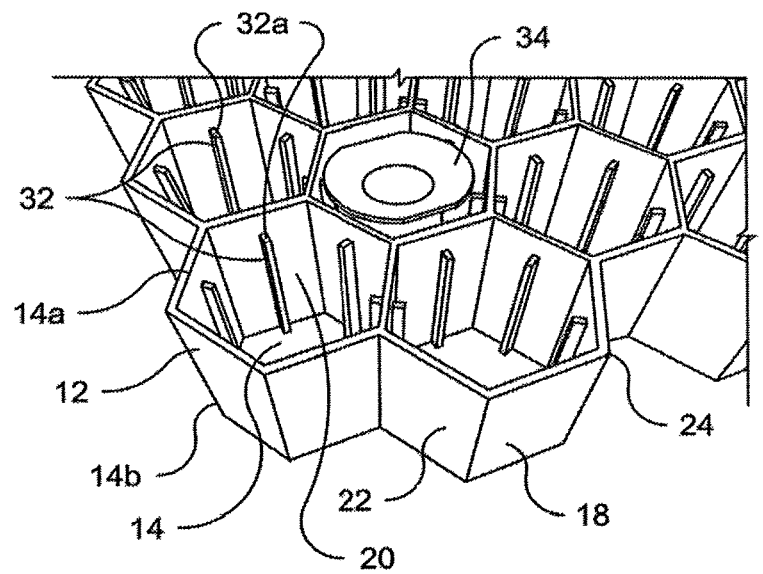
FIG. 7 is a top perspective, partial view of a syringe nest in accordance with another embodiment of the present invention with a syringe arranged in one chimney.

In another embodiment, as shown in FIG. 7, each retention member 32 is in the form of a longitudinally extending rib that does not extend to the first distal end 14a of each chimney 12 (i.e., the open top of the chimney 12). That is, each rib 32 extends from the second proximal end 14b toward the first distal end 14a, but terminates before reaching the first distal end 14a. The first end 32a of the rib 32 is thus below the plane of the first distal end 14a. As such, in use, the syringe 34 flange rests on the exposed surface (i.e., the first end 32a) of the one or more retention members 32 below the plane of the first distal end 14a of each chimney 12.

Figure 8:
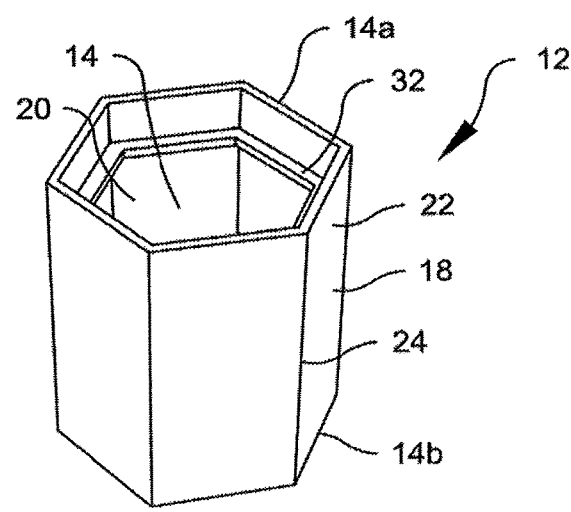
FIG. 8 is a top perspective view of a single chimney of a syringe nest in accordance with another embodiment of the present invention.
Figure 9A:
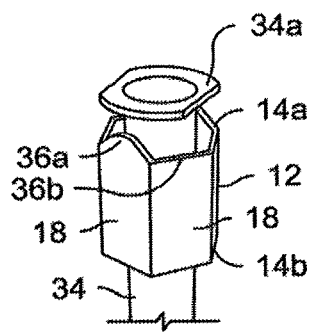
FIGS. 9A-9D are perspective views which depict the progression of insertion of a syringe into a single chimney of a syringe nest in accordance with another embodiment of the present invention.
Figure 9B:
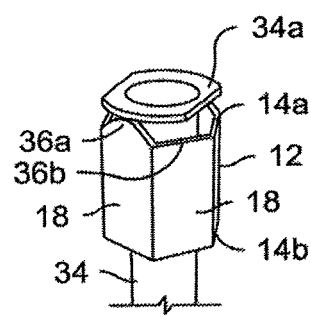
Figure 9C:
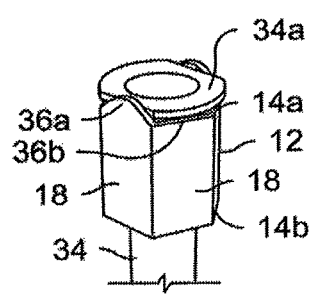
Figure 9D:
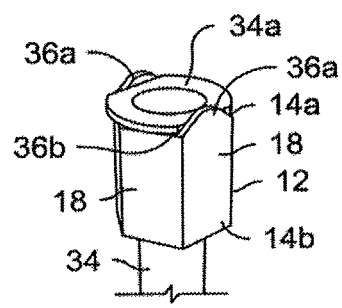

In another embodiment, as shown in FIG. 8, each retention member 32 is in the form of an annular shelf or shoulder extending inwardly from the interior surface 20 of the chimney 12 body 14 proximate the first distal end 14a. More particularly, the shelf 32 is formed below the plane of the first distal end 14a, such that, in use, the syringe 34 flange rests on the exposed surface of the shelf 32 below the plane of the first distal end 14a of each chimney 12. The shelf 32 may extend around only a portion of the interior periphery of the body 14, but preferably extends around the entire interior periphery thereof.

In another variation, as shown in FIGS. 9A-9D, cut-outs, ramps, or a cam geometry is implemented at the first distal end 14a (i.e., the top) of each chimney 12. The first open end 14a of each chimney 12 includes at least one cam 36a and at least one associated recess 36b, such that a syringe flange 34a contacts and travels over the at least one cam 36a and subsequently comes to rest in the at least one associated recess 36b. More particularly, at the first distal end 14a, a first plurality of the sidewalls 18 is provided as a rounded cam 36a, while a second plurality of the sidewalls 18 is provided with a cut-out 36b. Such a geometry allows a syringe flange 34a to initially contact and pass or travel over the cams 36a and then rest on the cut-outs 36b, such that the syringe flange 34a falls or cams into a centered position within a respective chimney 12 via gravity, mechanical assist (e.g., vibration), tilting, or any other similar movement, as shown in the progression depicted in FIGS. 9A-9D.

Two additional variations of cam geometries are shown in FIGS. 22A-22B and 23A-23E, respectively. The cams 50, 54 of the variation of FIGS. 22A-22B and 23A-23E function in a manner similar to the cams 36a of FIGS. 9A-9D. In the variation of FIGS. 22A-22B and 23A-23E, the cams 50, 54 are still formed at the first distal end 14a of each chimney 12, but are formed within the interior of the hexagonal chimney walls 18. This is beneficial because the overall geometry of the chimney 12 is more compact and will not interfere with a Tyvek seal, filling, etc.

Figure 22A:
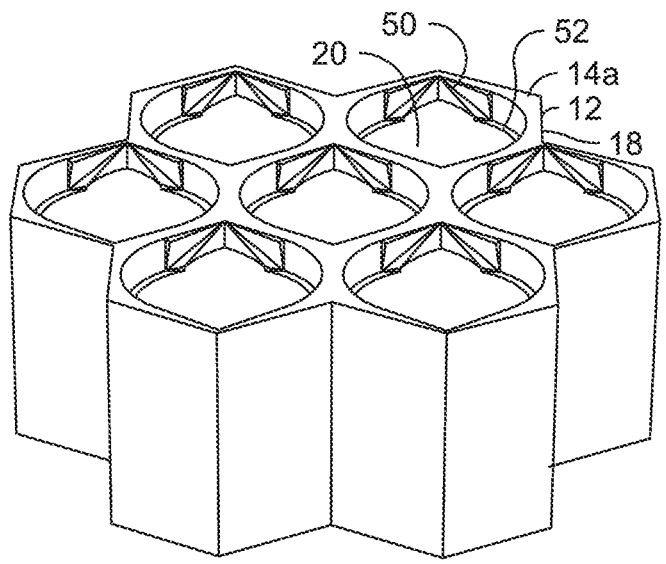
FIG. 22A is a perspective, partial view of a plurality of chimneys of a syringe nest in accordance with another embodiment of the present invention.
Figure 22B:
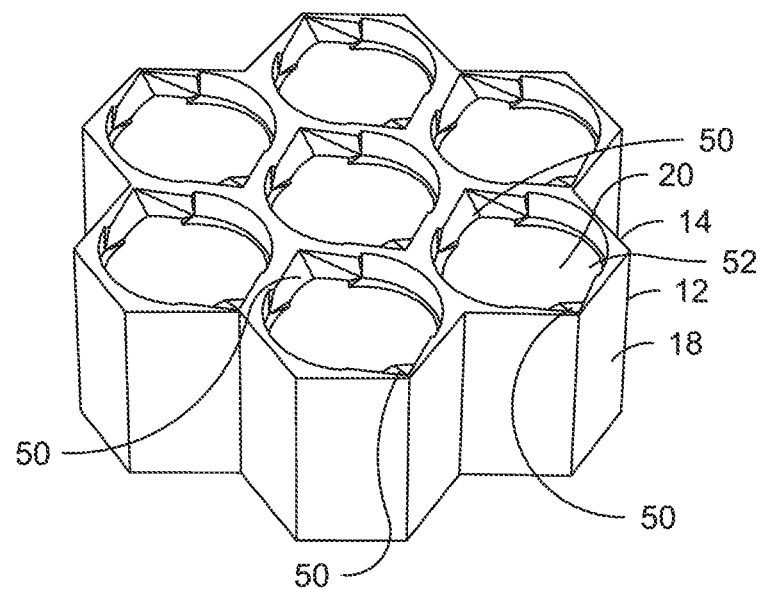
FIG. 22B is another perspective, partial view of the plurality of chimneys shown in FIG. 22A.
Figure 23A:
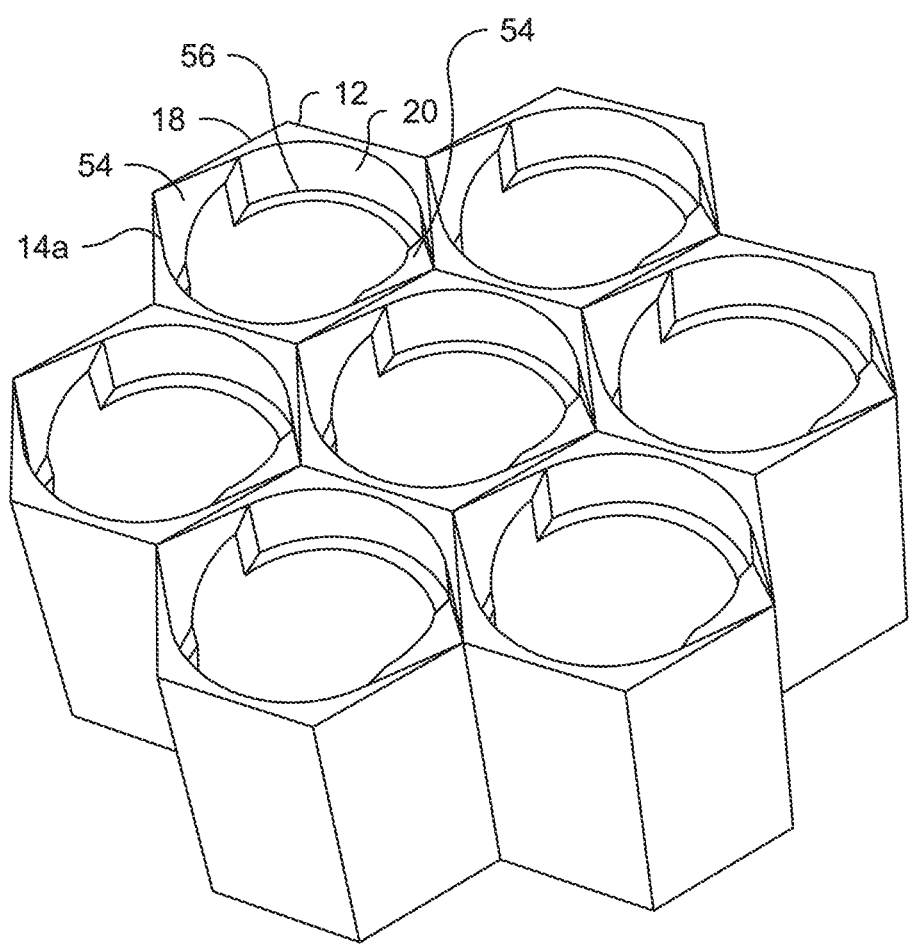
FIG. 23A is a perspective, partial view of a plurality of chimneys of a syringe nest in accordance with another embodiment of the present invention.
Figure 23B:
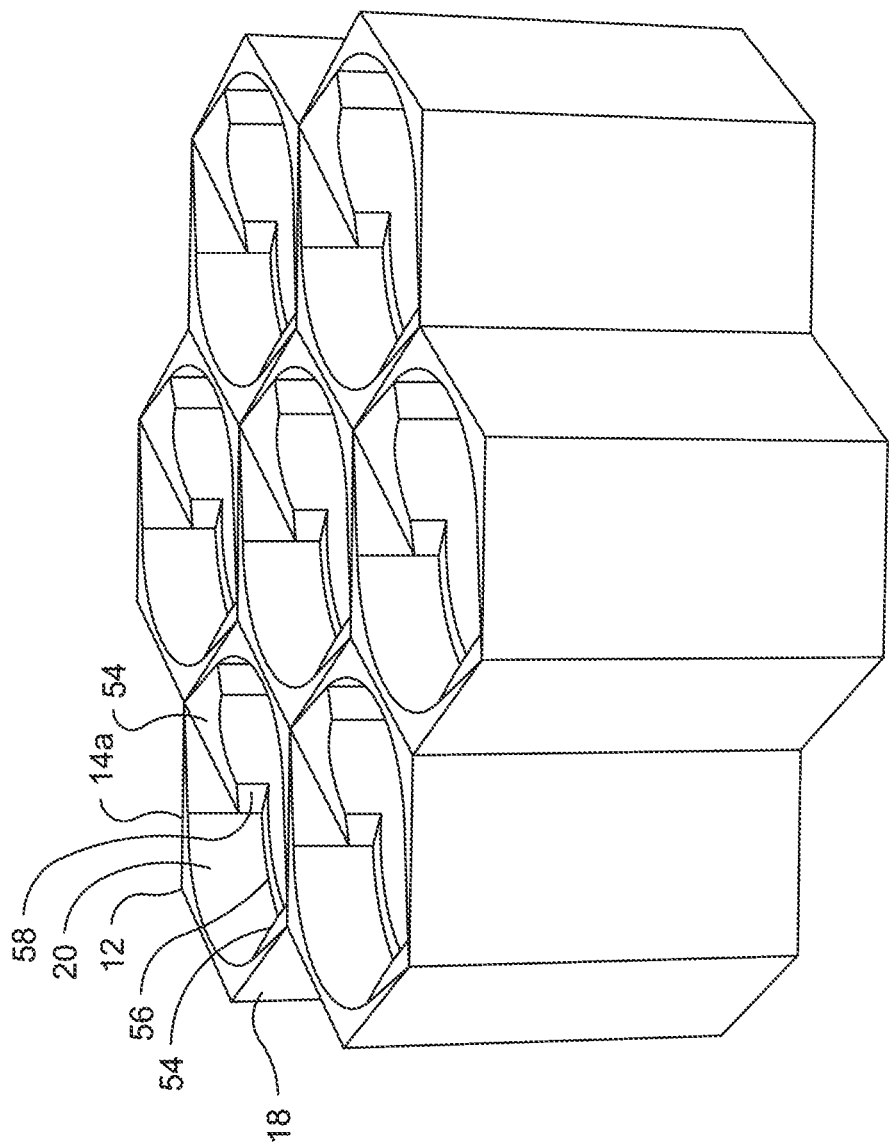
FIG. 23B is another perspective, partial view of the plurality of chimneys shown in FIG. 23A.
Figure 23C:
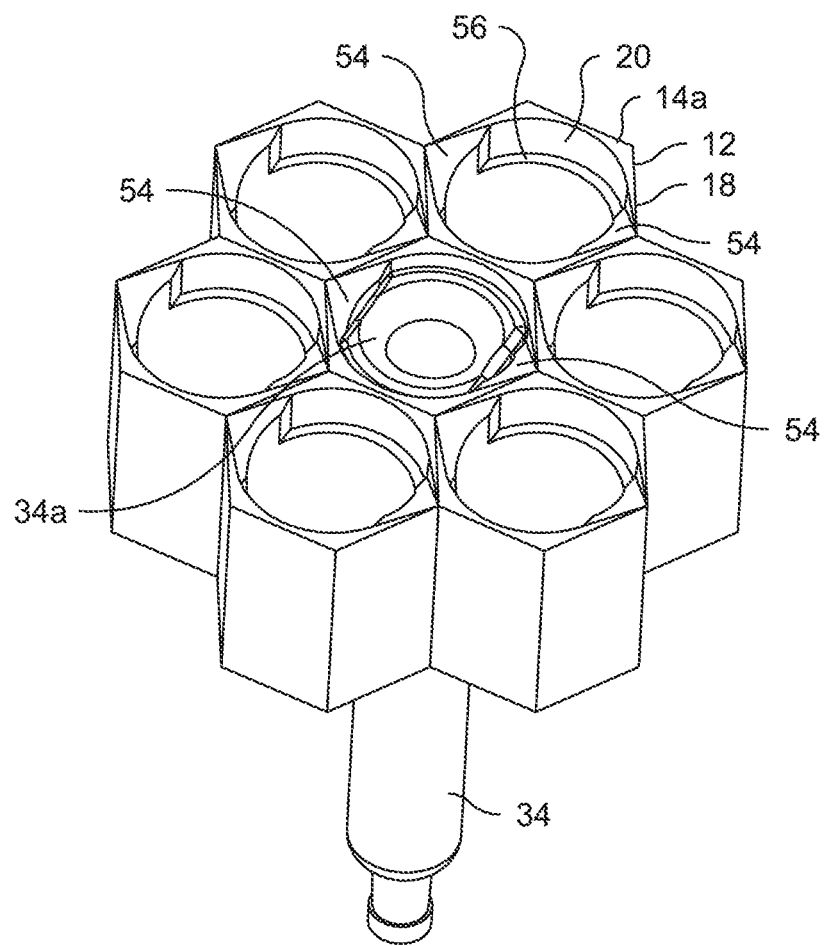
FIG. 23C is perspective, partial view of the plurality of chimneys shown in FIG. 23A with a syringe arranged in one chimney.
Figure 23D:
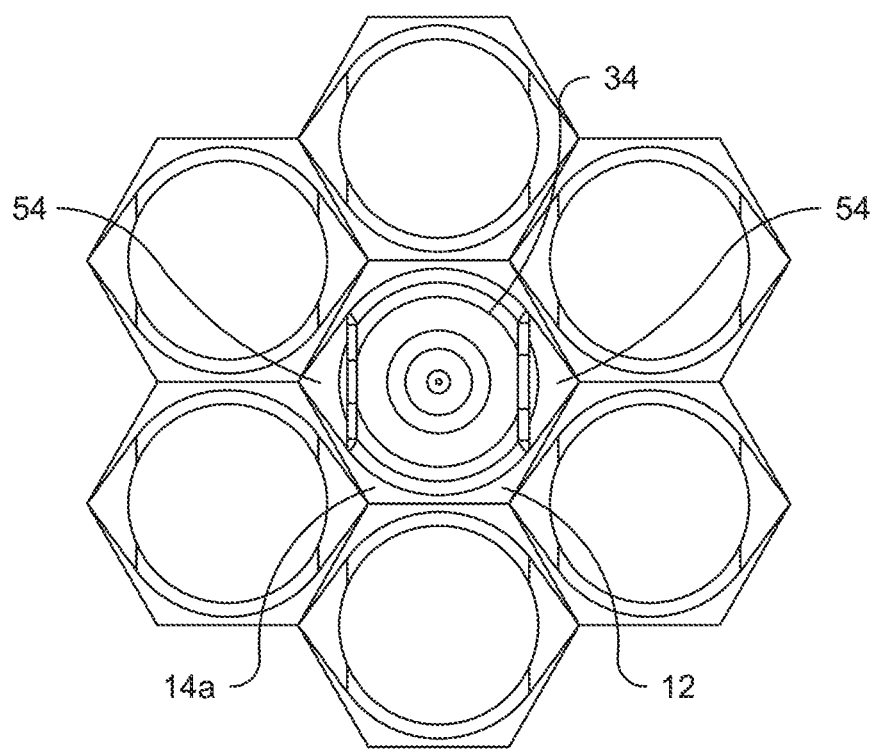
FIG. 23D is a top plan view of the plurality of chimneys shown in FIG. 23A with a syringe arranged in one chimney.
Figure 23E:
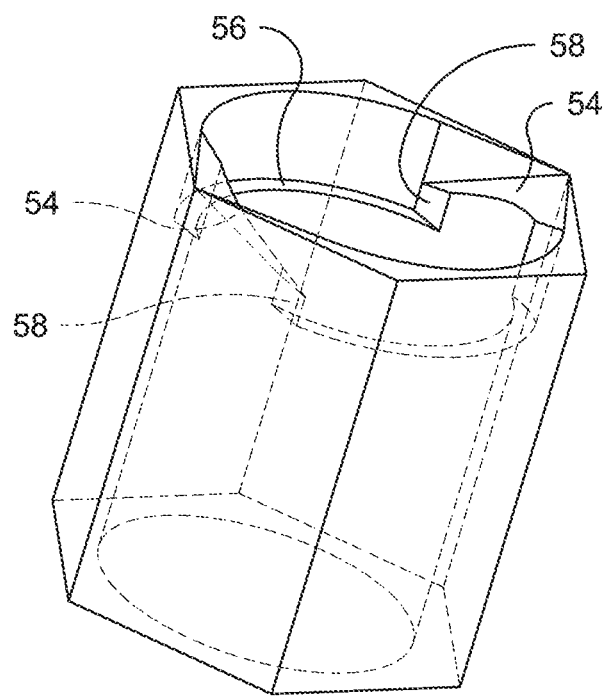
FIG. 23E is a perspective view of one chimney of the plurality of chimneys shown in FIG. 23A, with certain portions of the interior of the chimney shown in phantom.

In the cam geometry of FIGS. 22A-22B, first and second opposing and symmetrical pyramidal-shaped cams 50 are provided on the interior surface 20 of each chimney 12 at the first distal end 14a thereof. In use, when the syringe flange 34a is dropped into the chimney 12, it naturally drops into a flange-shaped recess 52 created by the cams 50, thus facilitating orientation of the syringes 34 to the requisite center-to-center distance D. Similar to the embodiment of FIGS. 9A-9D, the syringe flange 34a falls or cams into the centered position within a respective chimney 12 via gravity, mechanical assist (e.g., vibration), tilting, or any other movement that facilitates dropping of the flange 34a into the recess 52. The symmetrical cam design enables the possibility for the syringe 34 to balance across the top and/or edges of the opposing cams 50.

In the cam geometry of FIGS. 23A-23E, first and second asymmetric cams 54 are provided. The cams 54 are in the form of opposing inclined surfaces, upon which the syringe flange 34a may slide and/or rotate to travel down into a recess 56. Similar to the embodiment of FIGS. 9A-9D, the syringe flange 34a falls or cams into the centered position within a respective chimney 12 via gravity, mechanical assist (e.g., vibration), tilting, or any other movement that facilitates dropping of the flange 34a into the recess 56.

The asymmetrical cam design makes a more effective use of gravity, as the syringe flange 34a will always fall on an incline (i.e., the inclined cams 54) or into the recess 56. The asymmetrical cam design also includes a vertical drop 58 into the flange recess 56 that is below the bottom cam 54. The vertical drop 58 will prevent the syringe 34 from rotating back up the cams 54 (e.g., during transportation, filling, etc.) and moving out of tolerance of the necessary center-to-center distance D. It will be understood that such a vertical drop may also be included in the symmetrical cam design of FIGS. 22A-22B.

Figure 11A:
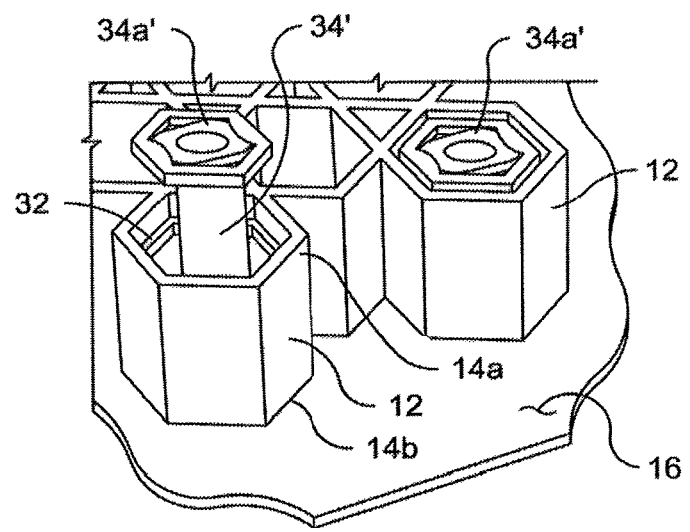
FIG. 11A is a partial top perspective view of a syringe nest in accordance with another embodiment of the present invention.
Figure 11B:
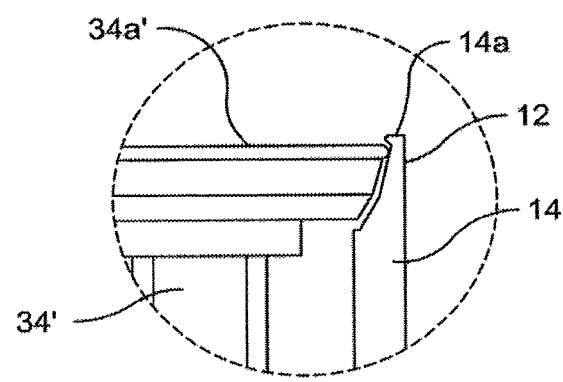
FIG. 11B is a partial cross-sectional view of a single chimney of the syringe nest of FIG. 11A.

In another embodiment, as shown in FIG. 11A, the present invention is directed to a syringe 34' having a flange 34a' of a shape and size that conforms with the shape of the chimney 12. That is, the flange 34a' has a generally hexagonal geometry or shape. Preferably, the interior periphery of the body 14 of the chimney 12 at its first end 14a is sized and contoured such that the syringe flange 34a' is pressure fit within the chimney 12, as shown in FIG. 11B. However, it will be understood that the chimney 12 may include one or more snap beads, ledges, bumps, ribs and the like to facilitate centering and capturing of the syringe flange 34a' within the chimney 12.

Figure 12:
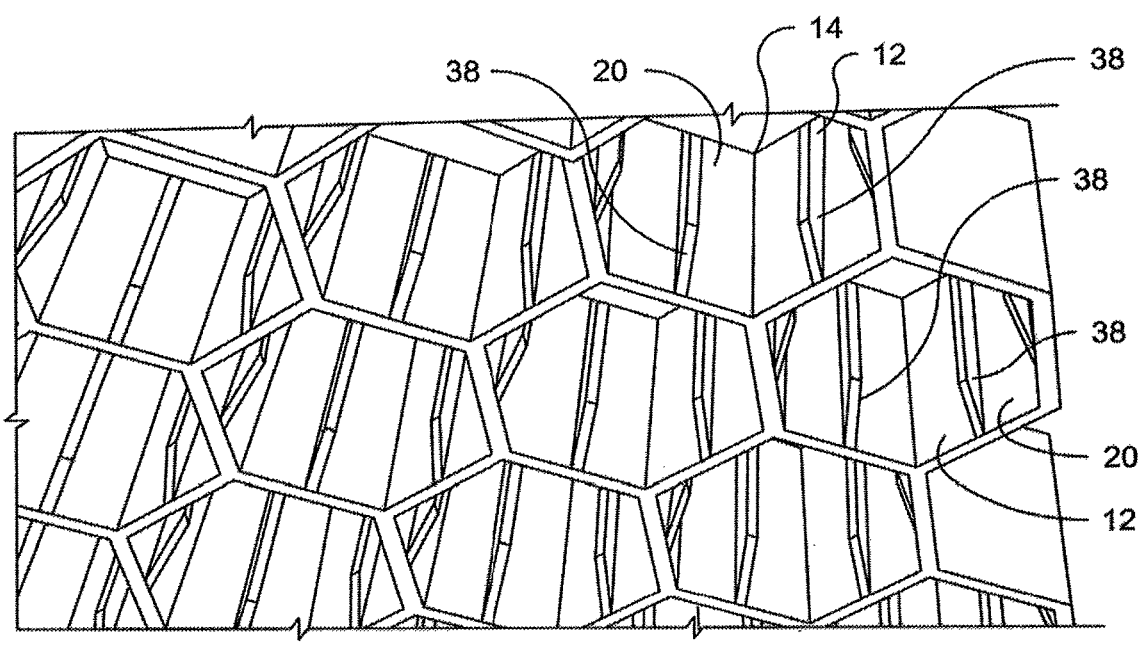
FIG. 12 is a top perspective, partial view of a syringe nest in accordance with another embodiment of the present invention.
Figure 13A:
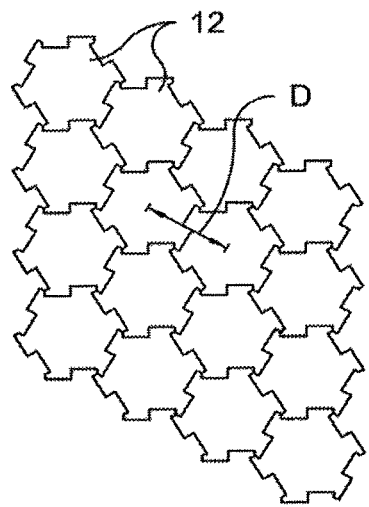
FIG. 13A-13D depicts schematic representations of various chimney geometries in accordance with another embodiment of the present invention.
Figure 13B:
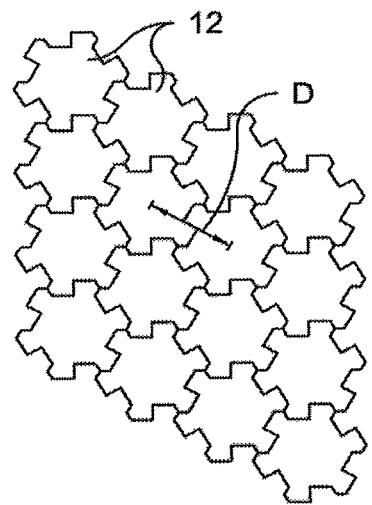
Figure 13C:
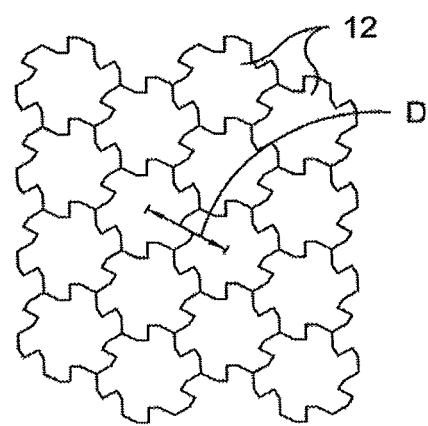
Figure 13D:
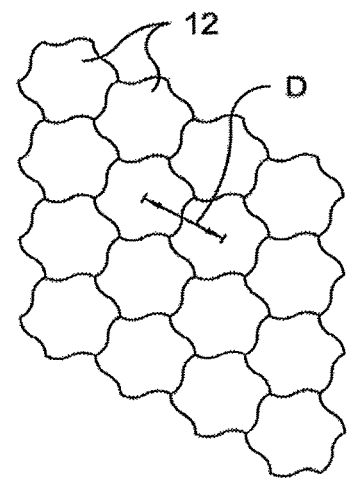

In addition to alignment geometry, it is also beneficial to ensure that a safety system, which has a diameter or width larger than that of the syringe 34 barrel, does not get caught on the bottom of the nest 10 during removal, a risk which is particularly present in embodiments utilizing a ledge or ribs within the chimneys 12. Accordingly, at least in such embodiments, each chimney 12 includes one or more chamfers 38 on the interior wall surface 20 to prevent catching on the chimney 12 during removal, as shown in FIG. 12.

FIGS. 13A-13D show various other embodiments of the chimney 12 geometry according to the present invention. In these embodiments, the chimneys 12 no longer have a hexagonal geometry, but are still arranged in a honeycomb pattern, so as to provide a surface on which the syringe 34 flange may rest, to maintain the predetermined center to center distance D, and to minimize sidewall thickness.

Figure 14:
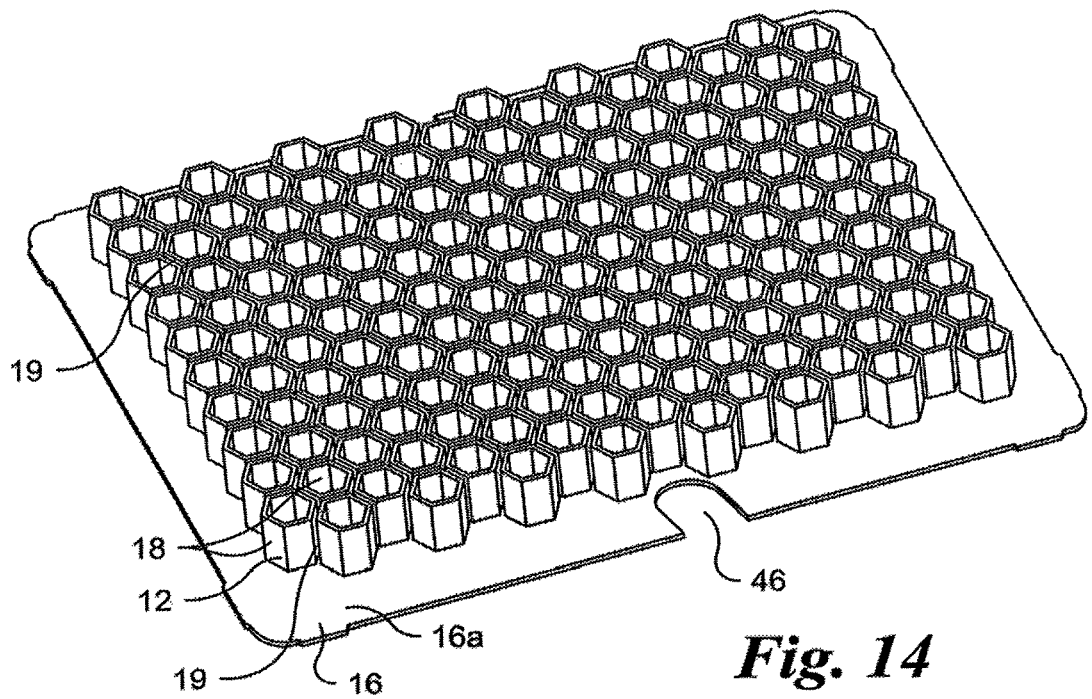
FIG. 14 is a top perspective view of a syringe nest in accordance with another embodiment of the present invention.
Figure 15:
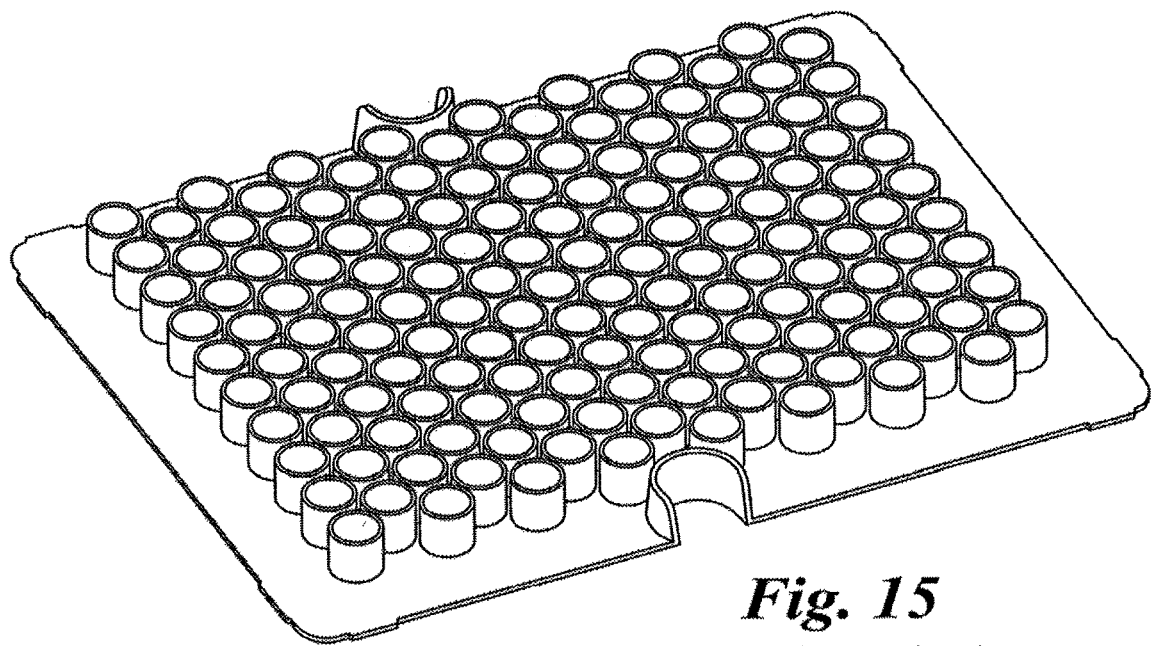
FIG. 15 is a top perspective view of a known syringe nest.

FIG. 14 shows another embodiment according to the present invention, in which the hexagonal chimneys 12 are arranged in a spaced-apart manner, such that the sidewalls 18 are not contiguous and a void or gap 19 surrounds each chimney 12. That is, aside from the chimneys 12 located on the outer periphery of the nest 10, a uniform gap 19 fully surrounds each chimney 12. The uniform gaps 19 between each chimney 12 result in uniform cooling of the mold. In contrast, the gaps between circular chimneys, as in the prior art nest of FIG. 15, would create varying thicknesses that are disadvantageous to mold heating and cooling.

Figure 16:
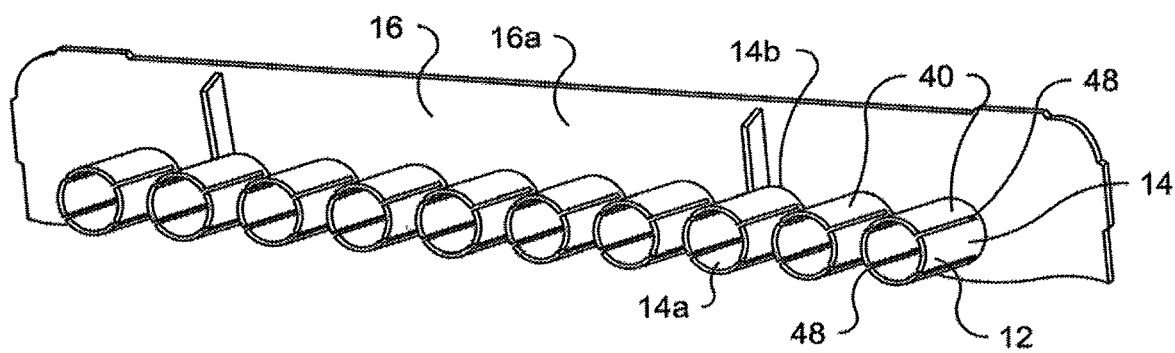
FIG. 16 is a perspective, partial view of a syringe nest in accordance with another embodiment of the present invention.

In another embodiment, shown in FIG. 16, the body 14 of each chimney 12 includes a plurality of longitudinally extending slits 48 which separate the body 14 into a plurality of spaced apart portions. One or more of the portions of the body 14 may be formed as flexing members 40 for improved securing and centering of the syringe 34 barrel and flange within a respective chimney 12. Centering and securing the syringes 34 in the chimneys 12 enables consistent filling and minimal movement of the syringes 34 during transit and/or shipping. The flexing members 40 may have a geometry, such as being angled, tapered or ramped from one end 14a, 14b of the body 14 of the chimney 12 toward the other end 14a, 14b, so as to allow for easy flexing of the members 40 and, in turn, easy insertion and removal of a syringe 34.

It will be understood that the concept of flexing members is not limited to a chimney 12 of a hexagonal geometry, but instead may be utilized on a chimney of various geometries, such as, for example, circular, square, triangular, and the like.

Figure 17:
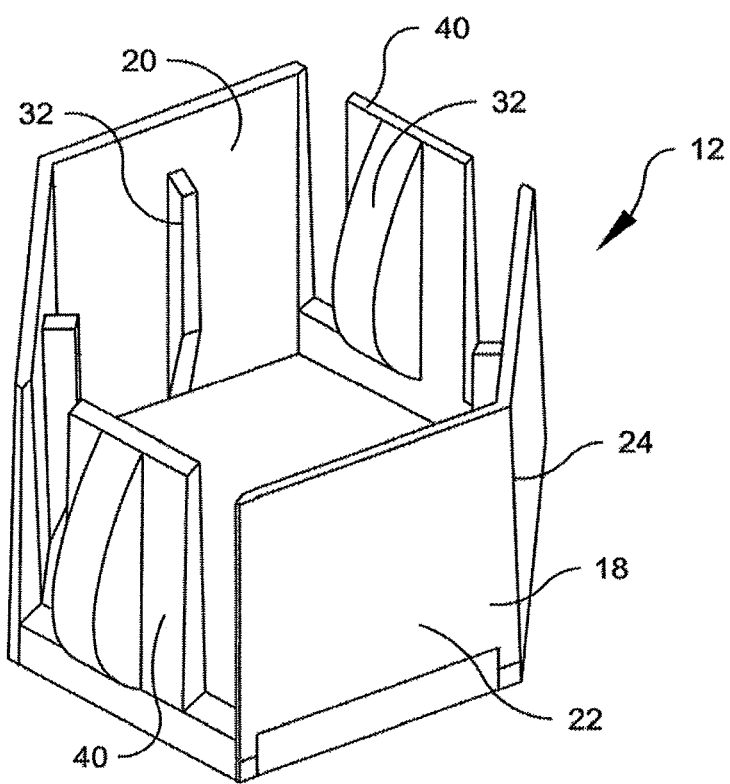
FIG. 17 is a perspective view of a single chimney of a syringe nest in accordance with another embodiment of the present invention.
Figure 18:
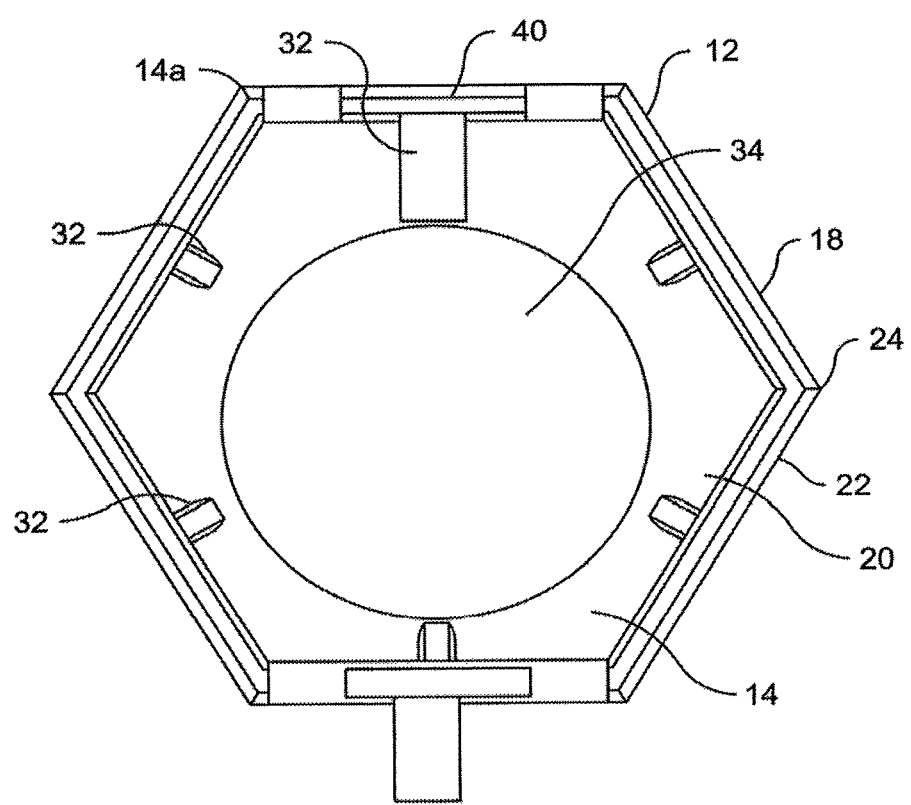
FIG. 18 is a top plan view of the chimney of FIG. 19 with a syringe arranged therein.
Figure 19:
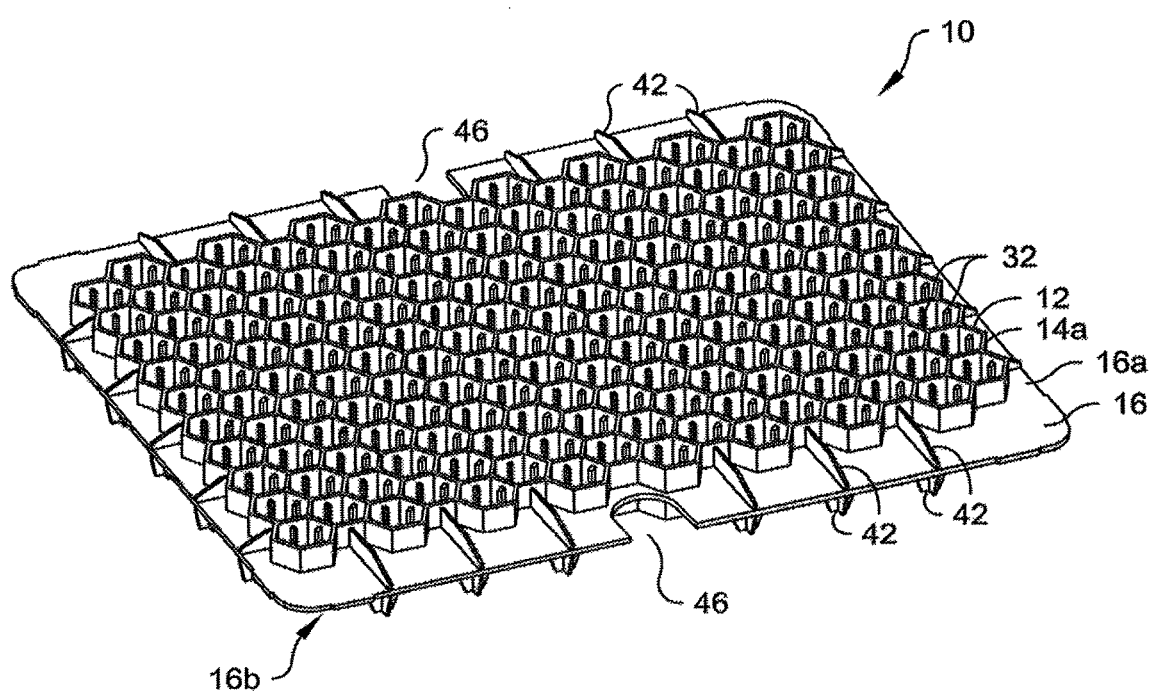
FIG. 19 is a side perspective view of a syringe nest in accordance with another embodiment of the present invention.
Figure 20:
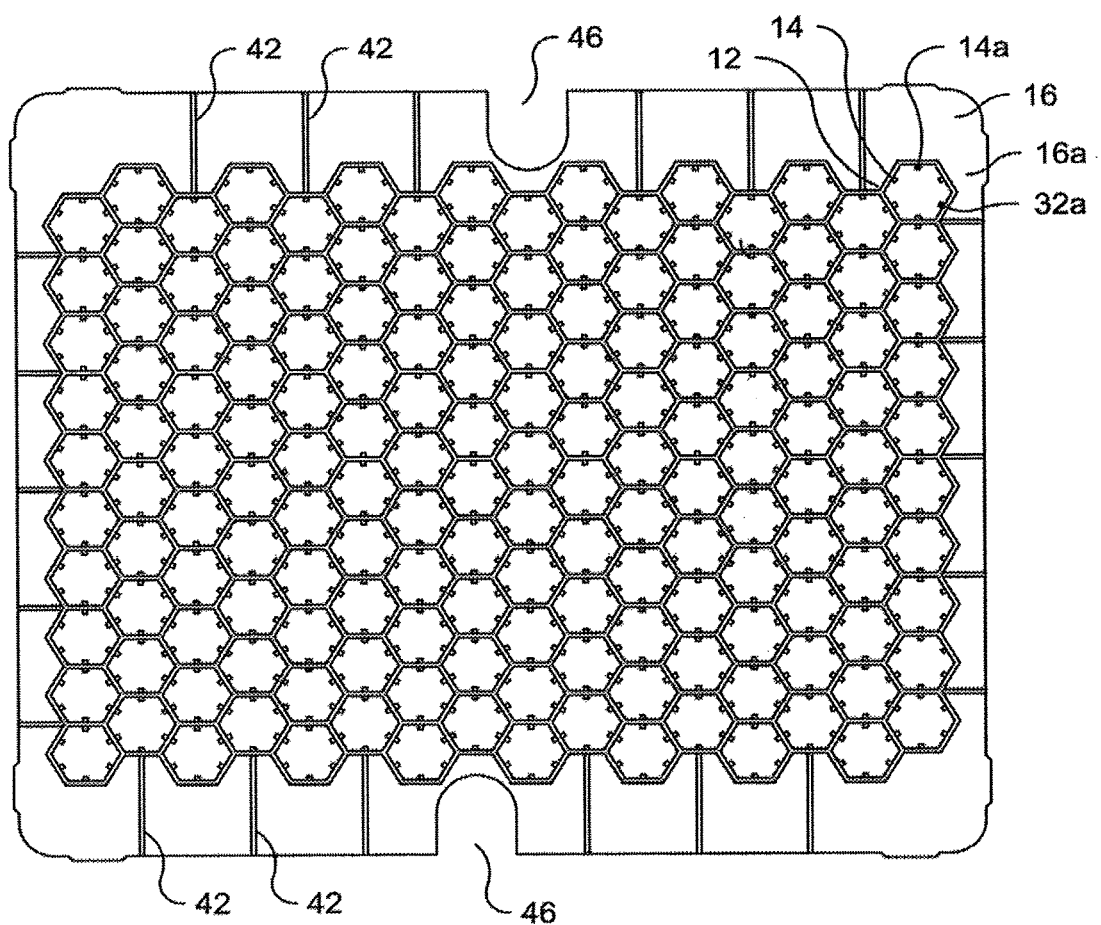
FIG. 20 is a top plan view of the syringe nest of FIG. 19.
Figure 21A:
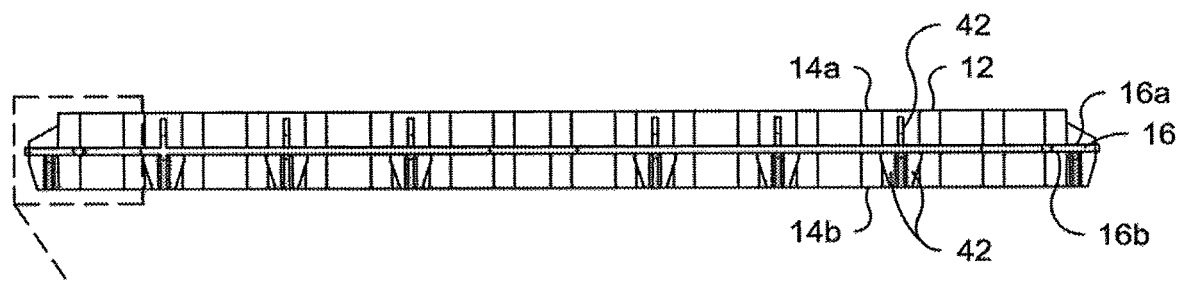
FIG. 21A is a side elevational view of the syringe nest of FIG. 19.
Figure 21B:
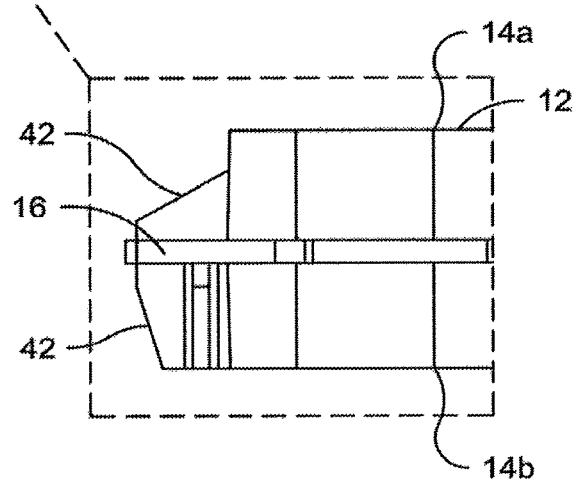
FIG. 21B is an enlarged view of a portion of the syringe nest shown in FIG. 21A.

In another embodiment, as shown in FIGS. 17-18, a chimney 12 may have only one flexing member 40 that provides support to a syringe 34 to be inserted therein from one direction, thereby intentionally off-centering the syringe 34 barrel within the chimney 12. However, to compensate, the chimney 12 pattern is similarly offset from center, such that once the syringes 34 are fully inserted within the chimneys 12, the syringes 34 are centered and aligned within the chimneys 12 for the filling position.

It will be appreciated by those skilled in the art that changes could be made to the embodiments described above without departing from the broad inventive concept thereof. It is to be understood, therefore, that the present invention is not limited to the particular embodiments disclosed, but it is intended to cover modifications within the spirit and scope of the appended claims.

We claim:

1. A syringe nest comprising:
   a planar base; and
   a plurality of nesting units extending from and interconnected by the planar base and having contiguous walls, each nesting unit comprising a hollow hexagonal body having a first open end and an opposing second open end, wherein the first open end of each hollow hexagonal body is distal from the planar base and the second open end is proximate the planar base.

2. The syringe nest of claim 1, wherein the nesting units are arranged in a point-to-point orientation.

3. The syringe nest of claim 2, further comprising a plurality of voids formed between the nesting units.

4. The syringe nest of claim 3, wherein the voids are triangular shaped voids.

5. The syringe nest of claim 3, further comprising an intermediate wall between first and second open ends of each of the voids.

6. The syringe nest of claim 1, wherein the nesting units are arranged in a honeycomb pattern with no voids formed between adjacent nesting units.

7. The syringe nest of claim 1, wherein the planar base is positioned at an intermediate position between the first and second open ends, such that a first portion of the hollow hexagonal body of each nesting unit extends distally from a first surface of the planar base and a second portion of the hollow hexagonal body of each nesting unit extends distally from a second surface of the planar base.

8. The syringe nest of claim 1, wherein the planar base includes a plurality of stiffening members extending from at least one peripheral edge of the planar base toward the plurality of nesting units.

9. The syringe nest of claim 8, wherein the plurality of stiffening members are formed on a first surface and a second surface of the planar base.

10. The syringe nest of claim 1, further comprising at least one retention member below a plane of the first open end.

11. The syringe nest of claim 1, wherein the hollow hexagonal body of each nesting unit includes a plurality of longitudinally extending slits separating the hollow hexagonal body into a plurality of spaced apart portions, at least one of the spaced apart portions being a flexing member.

12. The syringe nest of claim 1, wherein the first open end of each nesting unit includes at least one cam and at least one associated recess, such that a syringe flange contacts and travels over the at least one cam and subsequently comes to rest in the at least one associated recess.

13. The syringe nest of claim 12, wherein the first open end of each nesting unit includes a pair of opposing cams with the at least one recess being formed therebetween.

14. The syringe nest of claim 13, wherein the pair of opposing cams are symmetrical.

15. The syringe nest of claim 13, wherein the pair of opposing cams are asymmetrical inclined surfaces.

16. The syringe nest of claim 1, further comprising at least one retention member comprising at least one of a flange, a shelf, a rib, and/or spaced bumps.

17. The syringe nest of claim 16, wherein the at least one retention member comprises a radially inwardly extending longitudinal rib having a chamfered end.

18. The syringe nest of claim 1, wherein the second open end of each hollow hexagonal body is in the same plane as the planar base.

19. The syringe nest of claim 1, wherein the planar base surrounds the plurality of nesting units.

20. The syringe nest of claim 5, wherein the intermediate walls are in a different plane than the planar base.

21. A syringe nest comprising:
   a planar base; and
   a plurality of nesting units extending from and interconnected by the base, each nesting unit comprising a hollow hexagonal body having a first open end and an opposing second open end and at least one retention member comprising a radially inwardly extending longitudinal rib having a chamfered end.

* * * * *